United States Patent
Guo et al.

(10) Patent No.: US 7,169,251 B2
(45) Date of Patent: Jan. 30, 2007

(54) METHOD OF FORMING NANOFLUIDIC CHANNELS

(75) Inventors: Lingjie J Guo, Ann Arbor, MI (US); Xing Cheng, Ann Arbor, MI (US)

(73) Assignee: The Regents of the University of Michigan, Ann Harbor, MI (US)

( * ) Notice: Subject to any disclaimer, the term of this patent is extended or adjusted under 35 U.S.C. 154(b) by 253 days.

(21) Appl. No.: 10/436,657

(22) Filed: May 13, 2003

(65) Prior Publication Data

US 2003/0209314 A1    Nov. 13, 2003

Related U.S. Application Data

(60) Provisional application No. 60/379,878, filed on May 13, 2002.

(51) Int. Cl.
*B82B 3/00* (2006.01)
*B82B 1/00* (2006.01)
*B37B 37/02* (2006.01)

(52) U.S. Cl. ............... 156/292; 156/237; 156/247; 977/780; 977/840; 977/882

(58) Field of Classification Search ............... 156/230, 156/285, 286, 309.3, 308.2, 233, 237, 247, 156/290, 292, 297; 438/700, 706, 707, 710, 438/717, 757, 778; 436/180; 422/68.1, 422/100; 356/246, 344; 204/450–454; 977/712, 977/773, 774, 780, 782, 840, 880, 882, 887, 977/888; 430/314

See application file for complete search history.

(56) References Cited

U.S. PATENT DOCUMENTS

| | | | |
|---|---|---|---|
| 6,368,871 B1 * | 4/2002 | Christel et al. ............. | 436/180 |
| 6,593,065 B2 * | 7/2003 | Scherer ........................ | 977/887 |
| 6,635,163 B1 * | 10/2003 | Han et al. .................... | 204/450 |
| 6,802,489 B2 * | 10/2004 | Marr et al. ............. | 251/129.14 |
| 6,824,689 B2 * | 11/2004 | Wang et al. ................. | 977/782 |
| 6,860,956 B2 * | 3/2005 | Bao et al. .................... | 156/232 |
| 6,863,833 B1 * | 3/2005 | Bloom et al. ................... | 216/2 |
| 6,872,439 B2 * | 3/2005 | Fearing et al. ............... | 977/840 |
| 2002/0072243 A1 * | 6/2002 | Craighead et al. .......... | 438/745 |
| 2003/0212346 A1 * | 11/2003 | Yuzhakov et al. .......... | 600/584 |
| 2004/0033515 A1 * | 2/2004 | Cao et al. ....................... | 435/6 |
| 2004/0197843 A1 * | 10/2004 | Chou et al. ................ | 435/7.92 |

(Continued)

OTHER PUBLICATIONS

IBM Technical Disclosure Bulletin, Nonmetallic Nozzle Plate Assembly for Thermal Ink Jet Printheads, v. 34, N. 7B, pp. 274-277, Dec. 1, 1991.*

(Continued)

*Primary Examiner*—Sue A. Purvis
(74) *Attorney, Agent, or Firm*—Harness, Dickey & Pierce, P.L.C.

(57) ABSTRACT

A method of forming nanofluidic enclosed channels includes providing a first substrate having a layer of a first material disposed thereon. A plurality of nanoscale slots is formed along a second substrate using nanolithography, etching, or other disclosed techniques. The first substrate is then bonded to the second substrate such that the layer of the first material on the first substrate is adjacent the plurality of slots on the second substrate to define a plurality of enclosed nanofluidic channels therethrough.

7 Claims, 5 Drawing Sheets

U.S. PATENT DOCUMENTS

2005/0023156 A1* 2/2005 Ramsey et al. ............. 205/792

OTHER PUBLICATIONS

Tegenfeldt, J.O. et al., Near-Field Scanner for Moving Molecules, Physical Review Letters, v. 86, n. 7, pp. 1378-1381, Feb. 12, 2001.*

L. Jay Guo, Xing Cheng, & Chia-Fu Chou, "Fabrication of Size-Controllable Nanofluidic Channels by Nanoimprinting and Its Application for DNA Stretching", Nano Letters, vol. 4, No. 1, pp. 69-73, (2003).*

Choonsup Lee, Eui-Hyeok Yang, Nosang V. Myung, & Thomas George, "A Nanochannel Fabrication Technique without Nanolithography", Nano Letters, vol. 3, No. 10, pp. 1339-1340, (2003).*

Wanli Li, Jonas O Tegenfeldt, Lei Chen, Robert H Austin, Stephen Y Chou, Paul A Kohl, Jeff Krotine, and James C Strum, "Sacrificial polymers for nanofluidic channels in biological applications", Nanotechnology, vol. 14, pp. 578-583 (2003).*

S.Y. Chou, P.R. Krauss, W. Zhang, L.J. Guo, and L. Zhang, "Sub-10 nm imprint lithography and applications", J. Vac. Sci. Technol. B 15(6), pp. 2897-2904, (1997).

J.O. Tegenfeldt, O. Bakajin, Chia-Fu Chou, S.S. Chan, R. Austin, W. Fann, L. Liou, E. Chan, T. Duke and E.C. Cox, "Near-Field Scanner for Moving Molecules", Physical Review Letters, vol. 86, No. 7, pp. 1378-1381, (2001).

S.W. Turner, A.M. Perez, A. Lopez, and H.G. Craighead, "Monolithic nanofluid sieving structures for DNA manipulation", J. Vac. Sci. Technol. B, vol. 16(6), pp. 3835-3840, (2001).

M. Stjernstrom and J. Roeraade, "Method for fabrication of microfluidic systems in glass", J. Micromech. Microeng. 8, pp. 33-38, (1998).

H.P. Chou, C. Spence, A. Scherer and S. Quake, "A microfabricated device for sizing and sorting DNA molecules", Proc. Natl. Acad. Sci. USA, vol. 96, pp. 11-13, (1999).

H. Cao and Z. Yu, J. Wang, J.O. Tegenfeldt and R.H. Austin, E. Chen, W. Wu and S.Y. Chou, "Fabrication of 10 nm enclosed nanofluidic channels", Applied Physics Letters, vol. 81, No. 1, pp. 174-176, (2002).

S.R. Quake and A. Scherer, "From Micro- to Nanoabrication with Soft Materials", vol. 290 Science, www.sciencemag.org, pp. 1536-1540, (2000).

J. Han and H.G. Craighead, "Separation of Long DNA Molecules in a Microfabricated Entropic Tray Array", vol. 288 Science, www.sciencemag.org, pp. 1026-1029, (2000).

* cited by examiner

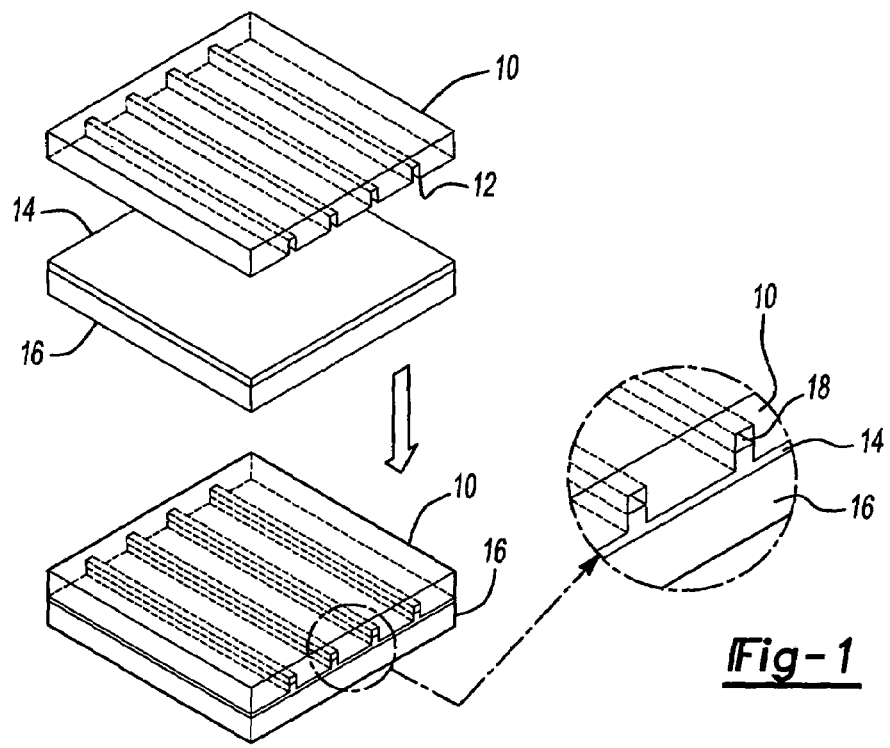
Fig-1
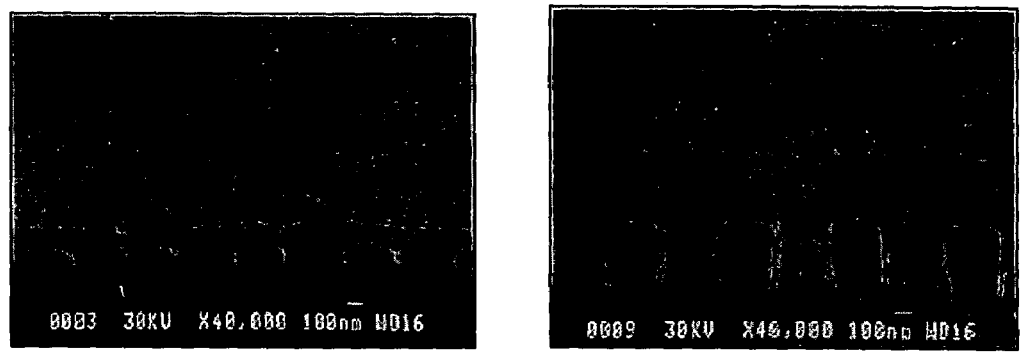
(a) Fig-2 (b)
stretched DNA
Fig-3

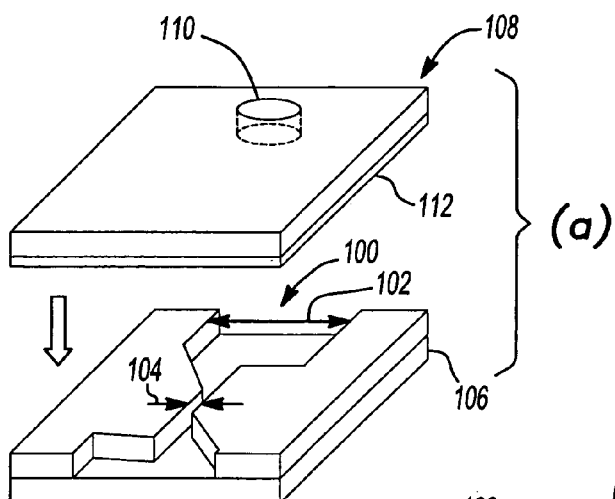
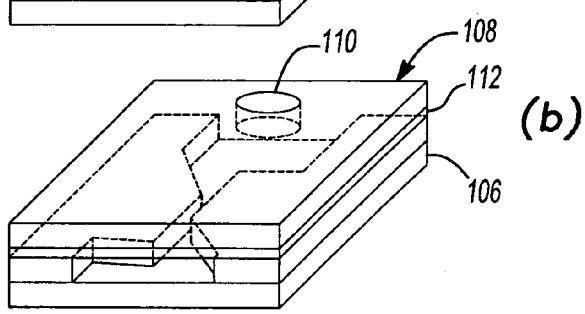
*Fig-5*
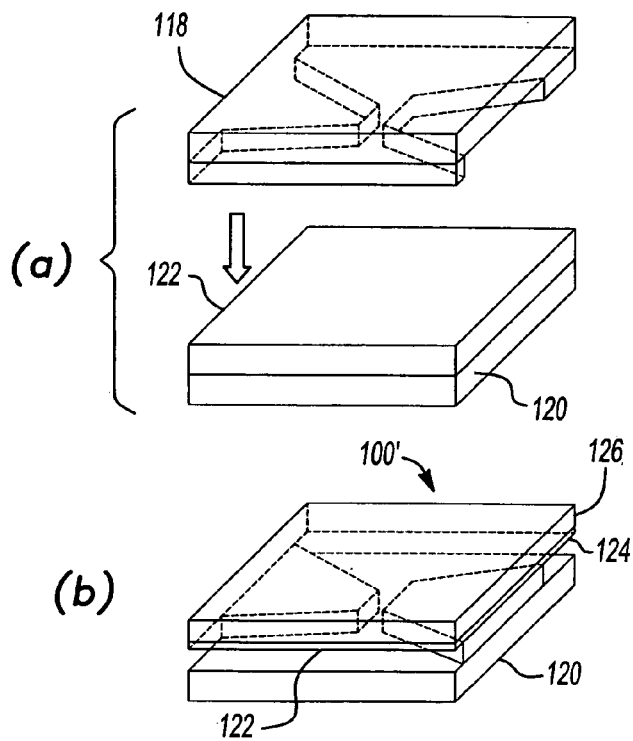
*Fig-6* ns of various types. The method of the present invention is
METHOD OF FORMING NANOFLUIDIC CHANNELS

CROSS-REFERENCE TO RELATED APPLICATIONS

This application claims the benefit of U.S. Provisional Application No. 60/379,878, filed on May 13, 2002. The disclosure of which is incorporated herein by reference.

FIELD OF THE INVENTION

The present invention generally relates to the construction of fluidic channels and, more particularly, relates to a simple and convenient method of constructing nanofluidic channels of various types. The method of the present invention is particularly useful in the manipulation and detection of bimolecular (especially DNA molecules) using nanostructured fluidic channels.

BACKGROUND OF THE INVENTION

Nano-scale fluidics (hereinafter "nanofluidic") is an emerging field of study that has significant technological advantages. For example, the interaction of biomolecules (such as DNA) with nanostructured channels having dimensions close to the persistence length of a molecule (~50 nm) permits an entirely new way of detecting and separating molecules. In fact, the unique fluid behavior at nanoscale dimension promises many new applications, assuming fabrication of nanofluidic channels can be simplified and made more cost effective.

Despite the relative ease of constructing nanoscale structures, the sealing of these nanoscale structures into functional nanofluidic channel devices often leads to many technological challenges. For instance, known methods of constructing sealed "micron-scale" fluidic channels typically include anodic bonding of a glass coverslip or soft elastomeric material to prefabricated channels on a substrate. The high temperature and high voltage typically used in the anodic bonding process greatly limit the process to commercial applications; while the bonding of soft elastomeric material, such as PDMS, to nanofluidic channels being about 100 nm or less in size often results in the partial or complete filling of the channel due to the rubber-like behavior of the soft elastomeric material.

As is known, sacrificial layer etching can also be used to form nanofluidic channels. However, the removal of this sacrificial layer in nano-channels is non-trivial. In fact, via holes are often necessary to reduce the time needed to remove the sacrificial layer to a reasonable duration, which consequently increases the device complexity and fabrication cost. Recent progress using non-uniform depositions, such as e-beam evaporation and sputtering, provides a flexible solution to this issue. Still this involves deposition machines and is a time-consuming and complex process that requires careful control of the non-uniformity during the deposition process.

Accordingly, there exists a need in the relevant art to provide a simple, convenient, and cost effective method of manufacturing nanofluidic channels. Furthermore, there exists a need in the relevant art to provide a simple, convenient, and cost effective method of fabricating nanofluidic channels having dimensions down to approximately tens of nanometers capable of being used in low-cost and high-volume manufacturing. Still further, there exists a need in the relevant art to overcome the disadvantages of the prior art.

SUMMARY OF THE INVENTION

It is therefore the object of this invention to provide a simple method of fabricating nanofluidic channels with dimensions down to tens of nanometers, which facilitates low-cost and high-volume manufacturing of nanofluidic channels for a wide range of applications.

According to the principles of the present invention, an advantageous method of forming nanofluidic enclosed channels is provided. The method includes providing a first substrate having a layer of a first material disposed thereon. A plurality of nanoscale slots is formed along a second substrate using nanolithography, etching, or other disclosed techniques. The first substrate is then bonded to the second substrate such that the layer of the first material on the first substrate is adjacent the plurality of slots on the second substrate to define a plurality of enclosed nanofluidic channels therethrough.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIG. 1 is a series of perspective views illustrating the method of fabricating nanofluidic channels according to the principles of the present invention;

FIGS. 2(a)–(b) is a series of photographs illustrating nanofluiclic channels fabricated by a polymer bonding technique representing a nanoscale depth according to the principles of the present invention;

FIG. 3 is a photograph illustrating application of the present invention in connection with DNA stretching;

FIGS. 5(a)–(b) is a series of perspective views illustrating the method of fabricating micro- and nanofluidic channels according to the principles of the present invention;

FIGS. 6(a)–(b) is a series of perspective views illustrating the method of fabricating all-polymer nanofluidic channels using a stamping method according to the principles of the present invention;

DETAILED DESCRIPTION OF THE PREFERRED EMBODIMENTS

Figure 4:
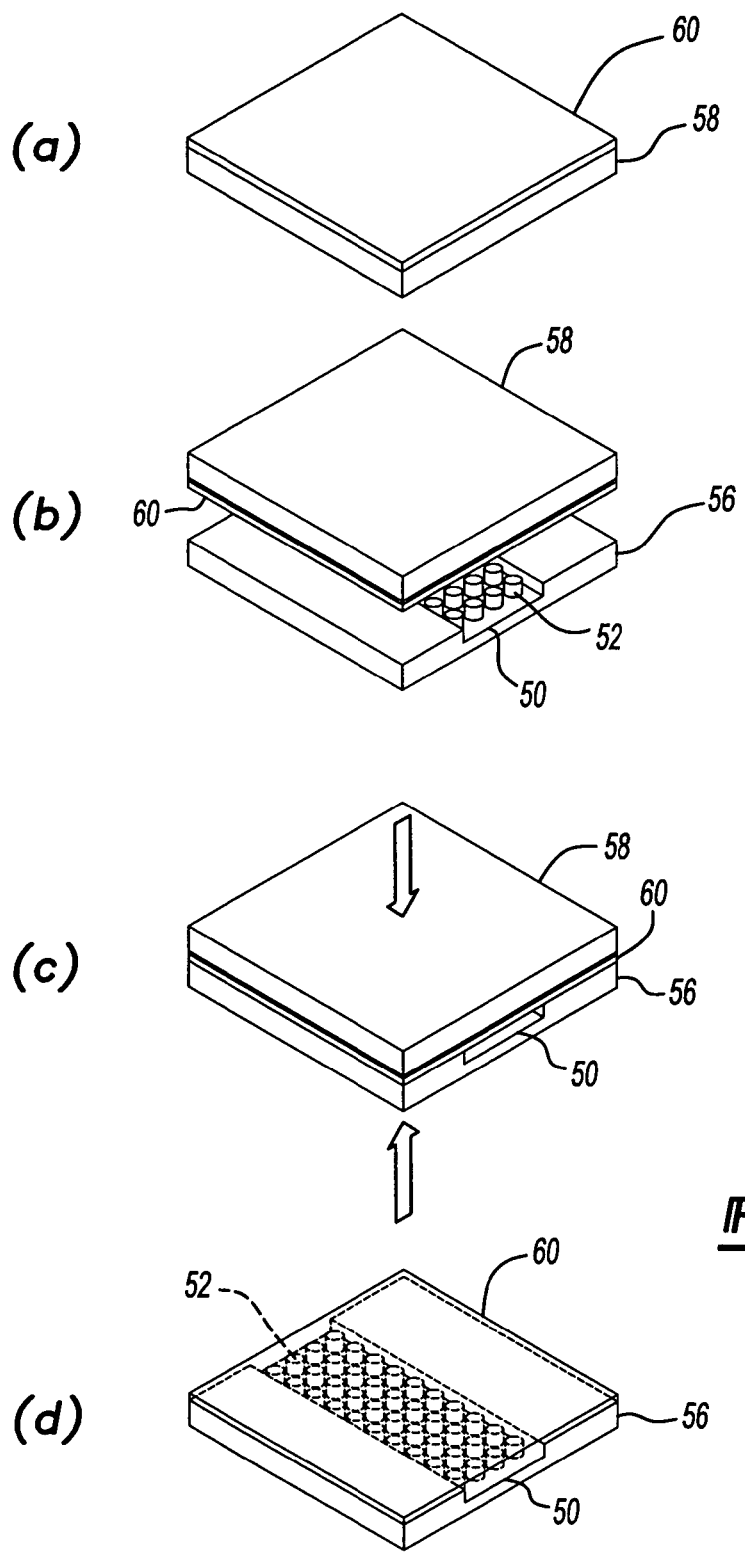
FIGS. 4(a)–(d) is a series of perspective views illustrating the method of fabricating nanofluidic channels with integrated artificial gel structure according to the principles of the present invention.

The following description of the preferred embodiment(s) is merely exemplary in nature and is in no way intended to limit the invention, its application, or uses.

According to the teachings of the present invention, a method is provided that includes directly forming fluidic channels by a 2-step nanoimprinting technique. With particular reference to FIG. 1, which illustrates a schematic of the preferred method, a nano-channel template 10 with nanoscale trenches 12 is fabricated by a first nanoimprinting and reactive ion etching (RIE) process in oxide. Then nano-channel template 10 is used as a mold (preferably without surfactant coating) to imprint into a thin polymer layer 14 on a substrate 16 through a second nanoimprinting process. A thickness of polymer layer 14 is carefully chosen such that polymer layer 14 will not completely fill nanoscale trenches 12 of nano-channel template 10. The portions of nanoscale trenches 12 of nano-channel template 10 that remain unfilled by polymer layer 14 define sealed channels 18. The lateral width dimension of sealed channels 18 is determined by the width of nanoscale trenches 12 of nano-channel template 10, while the height of sealed channels 18 is determined by the initial thickness of polymer layer (PMMA) 14 and/or by the initial depth of nanoscale trenches 12. By controlling the initial thickness of polymer layer 14 or the initial depth of nanoscale trenches 12, it is possible to accurately control the height of sealed channels 18, as illustrated in FIGS. 2(a)–(b). That is, in the current example, the width of sealed channels 18 is fixed at 350 nm. It should be understood, however, that the width of sealed channels 18 might be made to smaller dimensions rather straightforwardly. By choosing different initial widths and depths for nanoscale trenches 12, the volume of sealed channels 18 may be easily varied.

In this illustration, polymer layer 14 is made of PMMA, which is a thermal plastic material that possesses good optical properties and low auto-fluorescence level. Low auto-flourescence levels are particularly desirable for bimolecular detection using fluorescent labeling techniques. However, it should also be understood that the method of the present invention should not be regarded as being limited to the use of either PMMA or thermalplastic polymer for fluidic channel sealing. A wide range of materials, such as UV-curable, heat-curable polymers, sol-gel materials, and the like may be applied. With certain materials, the sealing of sealed channels 18 can be achieved at room temperature. Coating of the film onto the flat substrate can also be done by techniques other than spin coating, such as dip coating, and possibly spray coating depending on the properties of the material being used.

The fabrication of nano-fluidic channels by direct nanoimprinting techniques has many advantages. For example, nanoimprinting is generally regarded as being a relatively simple and cost effective process. The channels are sealed in one single nanoimprinting process. Additionally, the surface properties may be tailored by selecting different polymer materials or function. Furthermore, the complexity of fabricating the fluidic channels does not vary substantially as the size of the nanochannel changes. Therefore, in principle, the present method is equally applicable to the fabrication of larger-scale fluidic channels.

It is also possible to create a thick protection layer on top of the self-sealed nanofluidic channels by applying a second layer of coating that has solvent compatibility with the material used for sealing the channels. This technique also allows direct integration of optical element, such as near-field apertures on top of the nanofluidic channels, and optical waveguide to the side of the channel for optical excitations.

The methods described in the present application may be used in a wide variety of advantageous applications. For example, straight nanofluidic channels may be used in DNA stretching and, when combined with an integrated near-field scanner, they can be used for ultrahigh spatial resolution dynamic mapping of long chain polymers. An image of such application is provided in FIG. 3. Fluidic channels with dense arrays of nanoscale posts may also serve as artificial gels, which are commonly used in DNA electrophoresis. Such structures can be easily fabricated using a similar method as described above and a schematic of the fabrication process is illustrated in FIG. 4.

Briefly, with reference to FIG. 4, a channel 50 and nanoscale posts 52 may be formed and patterned inside a portion of a substrate 56 by nanolithography—such as electron beam lithography, deep UV lithography, or nanoimprinting technique—and reactive ion etching. Subsequently, a second substrate 58 is coated with a polymer 60 and is brought into contact and pressed against substrate 56 having fabricated channel 50 under elevated temperature. Channels 50 are sealed and good adhesion of polymer 60 to channel 50 is enhanced by the presence of the dense array of nanoscale posts 52 that act as artificial gels or entropic barriers for DNA strands. Substrate 58 may also be removed from the assembly when necessary if substrate 58 is made to have low surface energy.

In addition, electro-osmotic flow in nanofluidic channels can be used to create large pressure difference that is difficult to achieve with other techniques; this is very useful for fluidic pumping applications. In addition, nanofluidic channels are a new emerging area where many potential applications can be exploited. A simple and low cost fabrication technique will undoubtedly speed up such explorations. Further extension of this technique can create vertically integrated nanofluidic channels, and even more complex fluidic matrix.

Referring now to FIGS. 5(a)–(b), a schematic is provided that illustrates a simple technique of creating micro- and nanofluidic channels with device input and output according to the principles of the present invention. First, fluidic channels 100, having both micro-dimensions 102 and nanoscale dimensions 104, are defined on a substrate 106 by standard lithography and etching processes. A standard microscope coverslip 108 is also prepared that includes an inlet/outlet hole 110 etched through its entire thickness. A thin layer of polymer 112 (or other materials suitable for bonding and compatible with bimolecular detection) is uniformly coated over coverslip 108, by a conventional process such as spin coating. Coverslip 108 is flipped and brought on top of fluidic channels 100 and substrate 106. As seen in FIG. 5(b), under suitable temperature and pressure, a firm bond is formed between coverslip 108 and substrate 106, which at the same time seals fluidic channels 100. During this process, polymer material 112 will be displaced according to the pattern of fluidic channels 100. Similar as above, the height of nanofluidic channels 100 is determined by the initial etched channel depth and the amount of polymer 112 being squeezed into channels 100. Rigid coverslip 108 or other flat hard surface guarantees that no sagging will occur during nanochannel formation. It is anticipated that additional or auxiliary channels (not shown) may be positioned on sides of fluidic channels 100 to aid in the controlled displacement of polymer 112 during the bonding process. In the wide channel regions 102, auxiliary posts (not shown but similar to above) may be used to ensure that coverslip 108 does not bend and/or sag to block fluidic channels 100. Coverslip 108 preferably has a thickness of about 175 μm, which is compatible with many experimental setups using optical microscopes.

Alternatively, as seen in FIGS. 6(a)–(b), fluidic channels 100 on substrate 106 may be "stamped" out directly by using an imprinting technique using a template 118 and a substrate 120 having a first polymer layer 122. An additional polymer layer 124 and substrate 126 is then used to form an all-polymer fluidic channel 100'. The advantage of forming all-polymer fluid channel 100' is to be able to easily change its surface properties by surface chemical modification.

Figure 7:
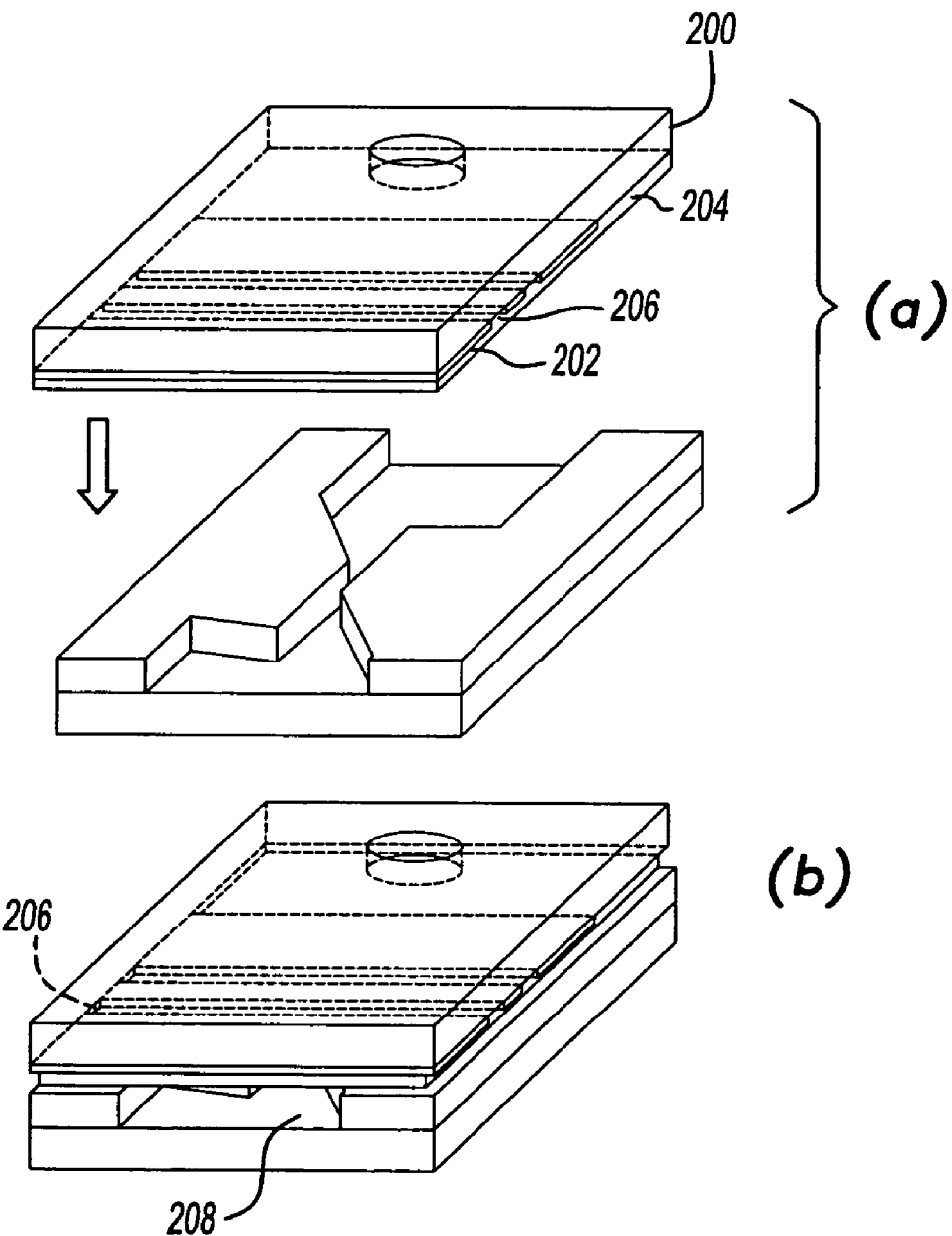
FIGS. 7(a)–(b) is a series of perspective views illustrating the method of fabricating nanofluidic channels and an optical slit according to the principles of the present invention.

Referring now to FIGS. 7(a)–(b), a simple approach of forming an (or an array of) optical near field slits above fluidic channels is illustrated. In this case, a coverslip 200 is first coated with metal 202 and patterned using Electron-beam lithography or nanoimprinting and etching, or alternatively by a lift-off process. Next, a polymer layer 204 is coated over metal layer 202 that has nanoscale opening slits 206. Subsequently, one may then employ the method described above in connection with FIG. 6 to form sealed fluidic channels 208. Laser beam incident from above metal nano-slits 206 will be attenuated and spatially localized due to the near-field effect, which can be used to provide highly localized excitations for fluorescent detection.

Figure 8:
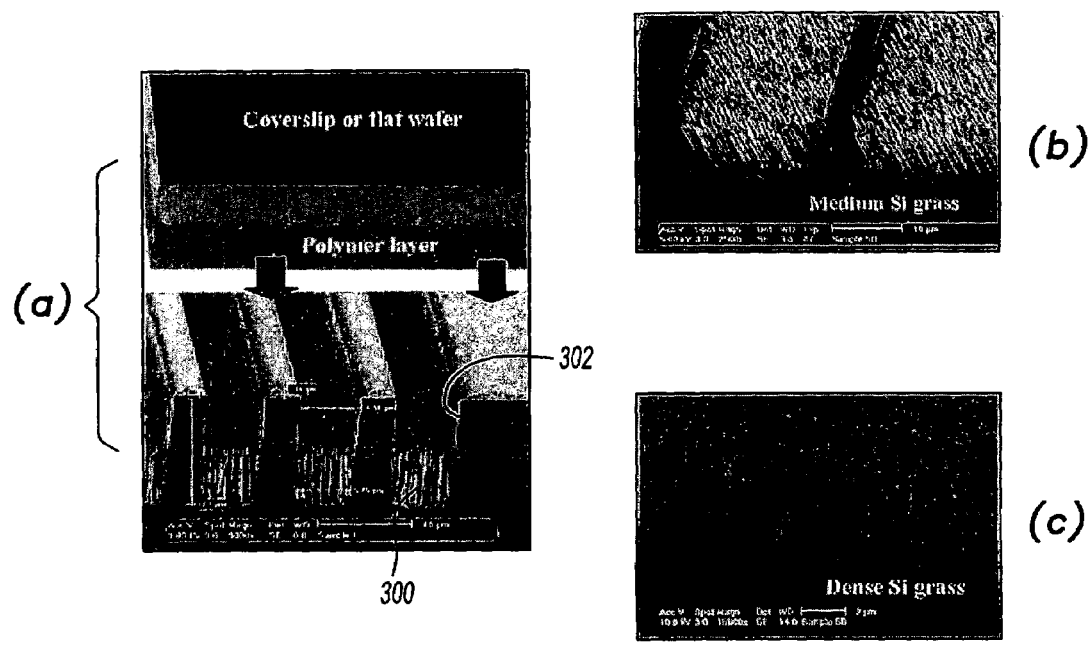
FIGS. 8(a)–(c) is a series of photographs, with portions shown schematically, illustrating nanofluidic channels having Si "grass" according to the principles of the present invention.

FIGS. 8(a)–(c) illustrate an alternative method to implement artificial gel structure that may be used in DNA electrophoresis. In this method, instead of patterning and etching posts with nanoscale separations as described above, a specially developed reactive ion etching process is used to create Si "grass" 300 in a trench region 302. The grass density can be controlled by the etching parameter as can be seen in FIGS. 8(b) and (c)). The position and separation between Si pillars 300 are random, mimicking a gel pore structure. Si grass 300 and channel 302 can be oxidized to facilitate electrophoresis process. To complete the fluidic channel, polymer material is used to provide the sealing from above as described above. Due to the soft nature of the polymer at temperatures above Tg, the tips of Si pillars 300 will penetrate into the polymer, which ensures that in DNA electrophoresis applications the biomolecules can only flow in between the narrow spacings between Si posts 300 at the bottom part of the channels.

Accordingly to the principles set forth above, the fabrication of nano-fluidic channels by direct nanoimprinting technique has many advantages. It is a simple and low-cost process. The channels are sealed in one single nanoimprinting process. The surface properties may be tailored by selecting different polymer materials or function. The complexity of the fluidic channel fabrication does not scale inversely to the size of the nano-channel. In principle, the present invention is also equally applicable to the fabrication of larger-scale fluidic channels.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of forming enclosed nanofluidic channels, said method comprising:
   providing a first substrate having a layer of a first material thereon;
   providing a second substrate;
   forming a slot of nanoscale depth along said second substrate, said slot being formed by nanolithography and etching; and
   bonding said first substrate to said second substrate such that said layer of said first material on said first substrate is adjacent said slot on said second substrate to define an enclosed nanofluidic channel therethrough.

2. The method according to claim 1, further comprising:
   removing said first substrate from said layer of said first material after said bonding.

3. The method according to claim 1, further comprising:
   forming a plurality of posts within said slot prior to said bonding of said first substrate to said second substrate.

4. The method according to claim 1 wherein said step of forming said slot along said second substrate includes forming a slot having both nanoscale and microscale dimensions.

5. The method according to claim 1, further comprising:
   applying a metallic coating to at least a portion of one of said first substrate and said second substrate prior to said bonding to define at least one optical slit.

6. The method according to claim 1 wherein at least one of said first substrate and said second substrate includes an aperture formed therethrough to permit fluid communication with said enclosed nanofluidic channel.

7. The method according to claim 1 wherein said step of forming said slot along said second substrate includes forming a slot having microscale width along at least a portion of said slot.

* * * * *